US00PP10597P

United States Patent [19]

Heims

[11] Patent Number: Plant 10,597

[45] Date of Patent: Sep. 8, 1998

[54] PULMONARIA PLANT NAMED 'BERRIES AND CREAM'

[75] Inventor: Dan M. Heims, Portland, Oreg.

[73] Assignee: Terra-Nova Nurseries, Inc., Tigard, Oreg.

[21] Appl. No.: 797,867

[22] Filed: Feb. 10, 1997

[51] Int. Cl.[6] ..... A01H 5/00

[52] U.S. Cl. ..... Plt./68.1

[58] Field of Search ..... Plt./68.1

*Primary Examiner*—Elizabeth C. Kemmerer

*Attorney, Agent, or Firm*—Klarquist Sparkman Campbell Leigh & Whinston, LLP

[57] ABSTRACT

A new and distinct variety of Pulmonaria having uniquely ruffled leaf margins and raspberry-pink flowers.

1 Drawing Sheet

The present invention relates to a new and distinct hybrid of Pulmonaria which originated as a cross-pollination of Pulmonaria 'Excalibur' and Pulmonaria 'Barfield Pink' in the Borage Family (Boraginaceae).

The new Pulmonaria is a result of a controlled cross of the aforementioned from a large selection of seedlings. Mother plants were retained to observe habit and to compare with their progeny. The new variety has been reproduced only by asexual propagation (division and tissue culture). Each of the progeny exhibits identical characteristics to the original plant and is unlike any Pulmonaria offered by any American nursery or book as evidenced by the following characteristics:

(1) Markedly ruffled leaves, silver with a thin green margin.

(2) Distinctive raspberry-pink flowers in spring.

Asexual propagation by division and tissue cultures done in Tigard, Oreg., shows that the foregoing characteristics and distinctions come true to form and are established and transmitted through succeeding propagations.

BRIEF DESCRIPTION OF THE PHOTOGRAPHS:

DETAILED PLANT DESCRIPTION

Figure 1:
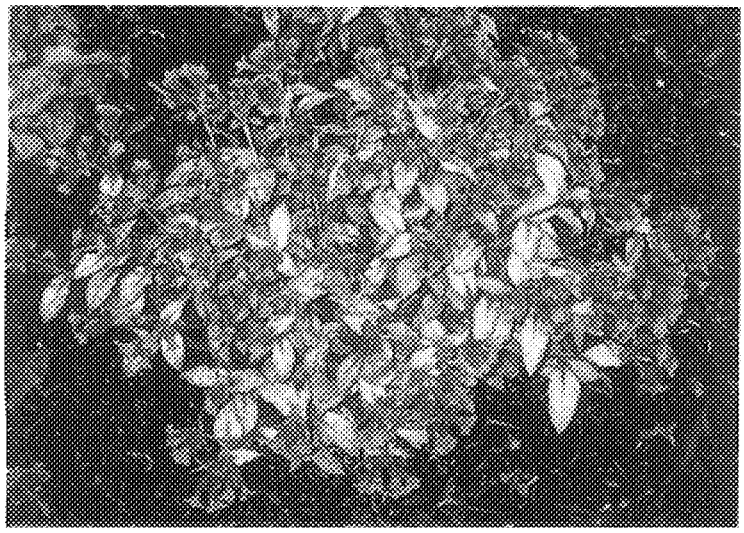
FIG. 1 is Pulmonaria 'Berries and Cream' in flower in early spring.
Figure 2:
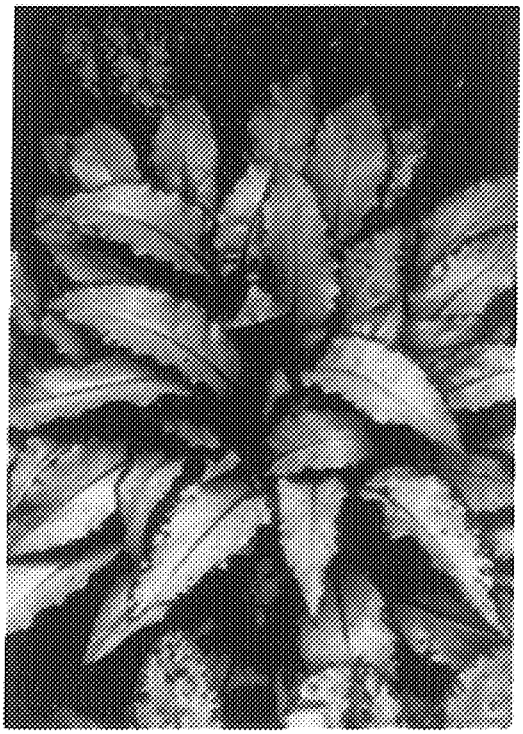
FIG. 2 is the plant in leaf, showing its summer foliage and ruffled leaf edge.

The following is a detailed description of the new Pulmonaria hybrid based on observations of specimens in Portland, Oreg. The color descriptions are all based on The Royal Horticultural Society Color Chart.

Foliage:

*Type.*—Herbaceous.
*Shape.*—Lanceolate.
*Length.*—to 35 cm (14 in).
*Width.*—to 6.5 cm (2 in).
*Petiole length.*—to 12 cm (4.75 in).

*Margins.*—Undulate, entire.
*Apex.*—Acute.
*Base.*—Angustate.
*Texture.*—Rough, reticulate.
*Leaf arrangement.*—Basal leaves, medium petioled.
*Venation.*—Reticulate-pinnate.

Flower:

*Corolla.*—5 petalled.
*Calyx.*—5 lobed.
*Flower type.*—Complete, calyx tube urn-shaped, stamens exserted.
*Flower size.*—1.25–1.5 cm ( 0.5–0.6 in).
*Blooming habit.*—Bracted, terminal forked cymes.
*Bloom period.*—Extended; February–April. Color Characteristics Foliage:

*Mature leaves upper surface.*—Spring–Fall: Greyed-green group 193B, bordered by green group 137C.
*Lower surface.*—Greyed-green group 193 A.

Flowers: Purple group 75C to Red-purple group 73C.

DESCRIPTION OF PARENT PLANTS

This Pulmonaria hybrid has characteristics which make it unique from its parents: Pulmonaria 'Excalibur' and Pulmonaria 'Barfield Pink'. Pulmonaria 'Excalibur', as described in U.S. Plant Pat. No. 8,958 and illustrated in the Terra-Nova Nurseries catalog of 1993 to 1997, has broader, less ruffled leaves with a larger green leaf margin and less brilliantly-colored flowers. Pulmonaria 'Barfield Pink', as described in the Fall 1995 catalog of Carolina Nurseries, 739 Gaillard Road, Moncks Corner, S.C. 29461, has broad, very dull, lightly spotted leaves and coral-pink flowers with white stripes. The influence of Pulmonaria 'Barfield Pink' is what conveys the ruffled leaf edge to the margin of Pulmonaria 'Berries and Cream'. No other Pulmonaria in commerce resembles Pulmonaria 'Berries and Cream'.

I claim:

1. A new and distinct hybrid of Pulmonaria plant substantially as shown and described, characterized by uniquely ruffled leaf margins and intensely pink flowers.

* * * * *